United States Patent [19]

Durnford et al.

[11] Patent Number: 5,324,524
[45] Date of Patent: Jun. 28, 1994

[54] YEAST DERIVED MITOGEN

[75] Inventors: Joyce M. Durnford; Richard S. Brody, both of Worthington, Ohio

[73] Assignee: American Home Products Corporation, New York, N.Y.

[21] Appl. No.: 695,656

[22] Filed: May 6, 1991

[51] Int. Cl.$^5$ .............................................. A61K 35/72
[52] U.S. Cl. .................................. 424/520; 424/195.1
[58] Field of Search ............................ 424/520, 195.1

[56] References Cited

U.S. PATENT DOCUMENTS

| 2,239,345 | 4/1941 | Sperti | 424/553 |
| 2,320,478 | 6/1943 | Sperti | 424/195.1 |
| 4,575,457 | 3/1986 | Mazarin | 424/52 |
| 4,942,031 | 7/1990 | Levin | 424/520 |

FOREIGN PATENT DOCUMENTS 4994M 5/1967 France .
1144876 of 0000 United Kingdom .

OTHER PUBLICATIONS

Chemical Abstracts, vol. 71, Nov. 3, 1969, No. 18, Columbus, Ohio, USA, Griffon, Henry "Dermatological ointment containing yeast cell membranes", p. 276, column 2.
Chemical Abstracts, vol. 98, Feb. 28, 1983, No. 9, Columbus, Ohio, USA, Mikami, Toshihiko et al. "Mitogenic effect of the mannans from Saccharomyces cerevisiae on mouse spleen lymphozytes" p. 476.
Chemical Abstracts, vol. 106, May 25, 1987, No. 21, Colubus, Ohio, USA, Nickerson, Deborah et al. "Stimulation of murine lymphozyte blastogenesis by mitogens in heat-killed Histoplasma capsulatum yeast cells", p. 565, column 2.
Goodson et al., "Augmentation of Some Aspects of Wound Healing by a Skin Respiratory Factor", Journal of Surgical Research, vol. 21, pp. 125–129 (1976).
Kaplan, "Acceleration of Wound Healing by a Live Yeast Cell Derivative", Arch. Surg., vol. 119, pp. 1005–1008 (1984).
Bentley et al., "Peptides from Live Yeast Cell Derivative Stimulate Wound Healing", Arch. Surg., vol. 125, pp. 641–646 (1990).
Subramanyam et al., "Effects of Preparation-H on Wound Healing in the Rectum of Man", Digestive Diseases and Sciences vol. 29, No. 9, pp. 829–832 (1984).
Hunt et al., "Studies on Inflammation and Wound Healing: Angiogenesis . . . Macrophages", Surgery vol. 96, No. 1, pp. 48–54 (1984).
Banda et al., "Isolation of a Nonmitogenic Angiogenesis Factor from Wound Fluid", Proc. Natl. Acad. Sci. vol. 79, pp. 7773–7777 (1982).
Vu et al., "Methods in Laboratory Investigation-An Evaluation of Methods . . . Angiogenesis", Laboratory Investigation vol. 53, No. 4, pp. 499–508 (1985).
Dusseau et al., "Stimulation of Angiogenesis by Adenosine on the Chick Chorioallantoic Membrane", Circulation Research vol. 59, No. 2, pp. 163–170 (1986).

*Primary Examiner*—Douglas W. Robinson
*Assistant Examiner*—Jean C. Witz
*Attorney, Agent, or Firm*—Sughrue, Mion, Zinn, Macpeak & Seas

[57] ABSTRACT

A substantially pure mitogen is obtained from yeast. Medicaments containing the same and methods of treatment using the same are described.

21 Claims, 3 Drawing Sheets

YEAST DERIVED MITOGEN

FIELD OF THE INVENTION

The invention relates to a high molecular weight yeast cell derived mitogen. The mitogen finds therapeutic utility in conditions that require cell proliferation, such as in wound healing.

BACKGROUND OF THE INVENTION

Factors obtained from yeast cells have been found to support a variety of effector activities. For example, one or more yeast factors stimulate the growth of other yeast cultures; one or more yeast factors stimulate the respiration of yeast cells; one or more yeast factors stimulate oxygen uptake in yeast, cultured fibroblasts, rat liver and rat abdominal skin; one or more yeast factors stimulate wound healing by the formation of collagen and new granulation tissue and the rate of epithelialization in rabbit ear wounds; and one or more yeast factors stimulate angiogenesis.

A crude extract containing one or more of said factors is obtainable by alcohol extraction of live yeast cells. The derivative obtained therefrom is a dark brown viscous fluid. The extract is commonly referred to as live yeast cell derivative.

Sperti, in U.S. Pat. No. 2,320,478, disclosed an alcoholic extract of yeast that was said to stimulate skin respiration. The active material was said to be substantially free of protein.

Mazarin, in U.S. Pat. No. 4,575,457, used a yeast extract obtained according to Sperti (supra) in a toothpaste which was claimed to be useful for improving the healing rate of gingivitis.

An alcoholic extract of yeast is a component of an over-the-counter preparation for treating hemorrhoids.

Kaplan (*Arch. Surg.* 119:1005–1008, 1984) stated that an alcoholic extract of yeast cells, prepared essentially as taught in Sperti (supra) appeared to enhance angiogenesis and epithelialization when applied as an ointment to wound sites.

Bentley et al. (*Arch. Surg.* 125:641–646, 1990) alleged to have obtained a low molecular weight mixture of peptides ranging in size from 6,000 to 17,000 daltons that showed angiogenic activity and stimulated wound healing. A crude alcoholic extract was centrifuged to remove cellular debris and the clarified supernatant was applied to a preparative gel filtration column. The resulting filtrate was analyzed by gel filtration, polyacrylamide electrophoresis and ion exchange chromatography.

Angiogenic activity was limited to low molecular weight peptides. Chemical analysis revealed that the extract contained a glucose disaccharide in which the glucose molecules are linked to each other by a 1→1 bond. Trehalose, a disaccharide which is abundant in yeast, is characterized by just such a bonding relationship.

In bioassays, the low molecular weight peptides were asserted to exhibit wound healing activity, however the concentration of peptides required to effect a biologic response were orders of magnitude greater than those required of other growth factors known in the art. Thus Bentley et al. concluded that the yeast derived peptides are not classic growth factors that act through cell surface receptors and a tyrosine kinase mechanism.

It is within this framework that the studies to be described hereinbelow were instigated. High molecular weight yeast derived factors were obtained in substantially pure form and said factors showed significant mitogenic activity.

SUMMARY OF THE INVENTION

One object of the invention is to provide a substantially pure mitogen obtained from yeast.

Another object of the invention is to provide methods of making said yeast derived mitogen.

A further object of the invention is to provide a method of treating hosts, preferably mammals and more preferably humans, with a composition comprising said mitogen.

The above and other objects have been attained in the development of a method for purifying from yeast a high molecular weight mitogen.

Figure 1:
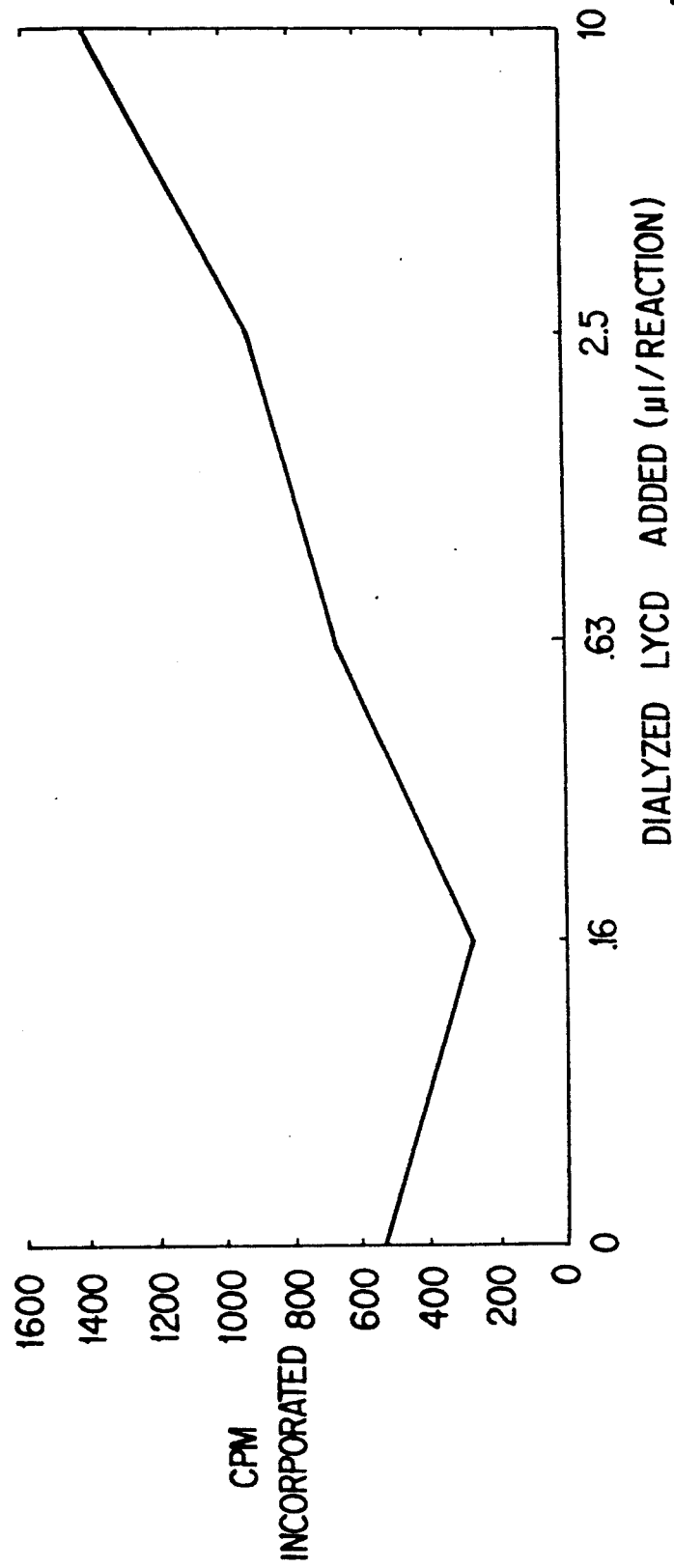
FIG. 1 depicts data obtained from the mitogenesis assay. Endothelial cells present a dose response of DNA incorporation to LYCD amount.

| Identifier | Time of Elution |
| --- | --- |
| 1 | 6.33 |
| 2 | 7.50 |
| 3 | 12.17 |
| 4 | 15.18 |
| 5 | 17.90 |
| 6 | 19.23 |
| 7 | 19.66 |
| 8 | 20.06 |
| 9 | 20.62 |
| 10 | 21.33 |
| 11 | 21.26 |
| 12 | 22.11 |
| 13 | 22.78 |
| 14 | 23.50 |
| 15 | 24.08 |
| 16 | 24.16 |
| 17 | 24.86 |
| 18 | 25.47 |
| 19 | 26.11 |
| 20 | 26.16 |
| 21 | 26.94 |
| 22 | 27.63 |
| 23 | 28.54 |
| 24 | 29.02 |
| 25 | 29.52 |
| 26 | 30.22 |
| 27 | 31.07 |
| 28 | 31.20 |
| 29 | 31.75 |
| 30 | 32.13 |
| 31 | 32.14 |
| 32 | 32.67 |
| 33 | 34.30 |
| 34 | 35.12 |
| 35 | 35.02 |
| 36 | 35.79 |
| 37 | 36.52 |
| 38 | 36.64 |

-continued

| Identifier | Time of Elution |
| --- | --- |
| 39 | 38.23 |
| 40 | 38.82 |
| 41 | 39.75 |
| 42 | 41.02 |
| 43 | 42.08 |
| 44 | 44.12 |
| 45 | 46.73 |
| 46 | 46.96 |
| 47 | 49.72 |
| 48 | 50.38 |
| 49 | 51.39 |
| 50 | 52.56 |
| 51 | 53.36 |
| 52 | 54.91 |
| 53 | 56.49 |
| 54 | 57.82 |
| 55 | 58.88 |
| 56 | 59.23 |
| 57 | 60.63 |
| 58 | 66.47 |
| 59 | 67.69 |
| 60 | 69.07 |
| 61 | 70.31 |
| 62 | 72.74 |
| 63 | 79.88 |

Fractions were collected and tested for mitogenic activity. The mitogenic response of 2.5 μl of each fraction was reported as the mean of four determinations. The negative control was 1312 cpm. The positive control, 10 μl of dialyzed clarified extract (Example 3) prepared from the reference standard of live yeast cell derivative was 7702 cpm.

DETAILED DESCRIPTION OF THE INVENTION

The subject matter of interest is a mitogen obtained by alcohol extraction of live yeast cells. (For purposes of this discussion, mitogen refers to one or more species with the cell proliferation capability described herein.) The molecular weight of the native mitogen is about or in excess of 600,000 daltons. The large size may reflect a subunit structure or aggregates of lower molecular weight species. When dialyzed yeast extract is passed over a gel exclusion column during liquid chromatography, the mitogen is recovered in a single well resolved fraction which elutes much earlier than the bulk of material applied to the column. The active fraction contains about 1% of the total material applied to the column and the mitogen is purified about 1,500-fold (hereinbelow 1,500-fold) from the crude extract based on the ratio of total protein and amino acids to the mitogenic activity of each sample. The mitogen fraction represents about 0.05% of the protein amino acids and 0.01% of the carbohydrate in the original extract. The molecule is stable to heat and cold. The mitogen in the dialyzed yeast extract is precipitated reversibly by acid. The data suggest that the active component is a glycoprotein.

Presence of the mitogen is determinable by bioassay, for example in a cell proliferation/DNA synthesis assay using cultured endothelial cells. With an assay of this nature, it is possible to track the active mitogen through the purification procedure.

Briefly, cells are exposed to serial dilutions of test samples and control reagents for a brief period of time, for example overnight. Then the cells are exposed to a labeled compound that is used to monitor cell division. An example of a labeled compound is a radioactively tagged nucleotide such as tritiated thymidine. In cells that are stimulated to undergo division, net DNA synthesis occurs and the labeled DNA precursor is incorporated into newly formed nucleic acids. The amount of radioactivity incorporated into DNA is determined using art-recognized methods, such as liquid scintillation counting. Generally, samples are run in replicates and an average level of incorporation per sample is determined from the readings. A convenient way for analyzing the data is to plot the average amount of label incorporated versus the volume of test reagent added to each reaction.

Mitogenic activity is detectable at about 0.001 mg/ml protein per assay. Mitogenic activity is detectable at 0.001 mg/ml protein in samples which are less than 10% pure. The assay is sensitive enough to detect mitogen at nanogram levels.

Each test sample to be evaluated for mitogenic activity must be found to be non-cytotoxic for the cultured cells. Thus, prior to analysis, the test samples are filter sterilized and the solution is made physiologic in composition, that is, pH of about 7.4 with the same attention being paid to salt concentration and other physiologic conditions.

The mitogen is obtainable from a variety of yeast strains, particularly of the genus *Saccharomyces*. Other suitable species include *S. diastaticus* and *S. steineri*. Particularly useful is Brewer's yeast, *S. cerevisiae*, which is available commercially, such as from Gist-Brocades Food Ingredients East Brunswick, N.J. and Universal Foods Corporation Willow Grove, Pa. Live yeast cells are added to ethanol and the slurry is incubated at about 70° C. for about three hours or more. The mixture is cooled and the particulate matter is removed. The filtrate is cleared with charcoal or other clarifying agent. Following removal of the clearing agent, the alcohol is evaporated under vacuum yielding a viscous brown syrup.

A common first treatment of further purification is clarification of the syrup. The crude extract is diluted with water and clarified by centrifugation. The clarified extract is then dialyzed at about 4° C. in about 1,000 molecular weight cut-off tubing (spectrum) against water or a suitable physiologic buffer. The clarified extract may also be dialyzed using 500,000 MW cut-off tubing (spectrum) as an effective purification step. The dialysate contains substantially pure mitogen, which can be purified even further.

Optionally, the pH of the dialysate is lowered to below or about 4 to enable precipitation of the mitogen. Following an incubation of about an hour, the precipitate is removed and dissolved in a physiologic buffer.

A method that obtains 1,500-fold purification is size exclusion chromatography. The dialysate or dissolved acid precipitate is separated over a gel filtration matrix that distinguishes molecules according to size. An example of this type of chromatography is the column format Fast Protein Liquid Chromatography (FPLC) system of Pharmacia (Piscataway, N.J.) using a cross-linked agarose matrix, such as Superose 12 HR 10/30 which comprises agarose beads of about 10 μm with an exclusion limit of 300,000 molecular weight. Using that system, essentially all of the mitogenic activity is recovered in the void volume indicating that the mitogen has a molecular weight of greater than 300,000. The active peak co-elutes with blue dextran (molecular weight of approximately 2,000,000) and elutes measurably before thyroglobulin which has a molecular weight of 669,000.

The molecular weight of the native mitogen is therefore likely to be greater than that of thyroglobulin.

The chromatographic fractions containing mitogenic activity do not show an ultraviolet absorbance maximum ($A_{max}$) at approximately 280 nm which is typical for proteins. Instead there is a continuous rise in absorption as the wavelength is changed from 320 nm to 240 nm. The mitogen has an absorbance at 280 nm that is more than 10 times greater than that of an equivalent weight of an average protein. The mitogen may have a large aromatic content, and hence an unusually high absorbance, or much of the $A_{280}$ peak is not due to protein absorption.

The mitogen is broadly temperature resistant. Activity is not affected by heat treatment at 100° C. for five minutes or by freezing prior to and during lyophilization. Thus the mitogen is stored conveniently in a dry state following lyophilization.

The material obtained following dialysis and Superose 12 HR 10/30 chromatography contains protein and carbohydrate in approximately a 3:1 ratio.

Presence of carbohydrate is determinable by standard procedures. For example, 70 $\mu$l of 80% phenol is added to 2 ml of sample. Then 5 ml of concentrated sulfuric acid is added and the solution is allowed to incubate at room temperature for 10 minutes. The absorbance at 490 nm is ascertained in a spectrophotometer.

Presence of protein is determinable by standard procedures such as the ninhydrin assay and also by the bicinchoninic acid/copper sulfate reagent obtained commercially from Pierce and used according to manufacturer's instructions. If the sample is to be hydrolyzed, then 250 $\mu$l of sample is added to a polypropylene tube and the tube is heated at 150° C. to dryness. To each tube is added 150 $\mu$l of 13.5M NaOH and the solution is autoclaved for twenty minutes at 15 PSI (fast exhaust). The tubes are cooled and 250 $\mu$l of concentrated acetic acid are added to each tube. Then, 500 $\mu$l of ninhydrin reagent (Pierce) are added to the tube which is then heated for fifteen minutes at 100° C. in a heating block. The sample is cooled immediately and 2.5 ml of 50% ethanol are added to each tube. The optical density at 570 nm is read using deionized water as a blank. A 500 $\mu$g/ml solution of leucine can serve as a control. If the sample is not hydrolyzed, then the steps prior to addition of a ninhydrin reagent are not required. A 400 $\mu$l volume of non-hydrolyzed sample is added to the polypropylene tube and ninhydrin reagent is mixed therewith.

At this stage of purification, that is, following centrifugation, dialysis, optional acid precipitation and size exclusion high pressure liquid chromatography, a 1,500-fold level of purification is achieved. The purification can be extended, for example, to include additional chromatography such as passage over other gel filtration columns, ion exchange columns, affinity columns, hydrophobic interaction columns or reverse phase columns. Thus the dialysate or dissolved acid precipitate is applied to a Bio-Sil TSK 125 column (Bio-Rad) or G2000 SW column (Toso-Haas) which is comprised of a porous hydrophilic silica support designed for size separation. The mitogen binds weakly to this column.

The mitogen may be highly anionic as the active components bind tightly to a Mono Q anion exchange column (Pharmacia LKB).

Reverse phase chromatography is useful for separating hydrophobic compounds. Generally the matrix comprises a silica gel, with beads in the $\mu$m size range and a pore size on the order of 100–300 Å, with various combinations of C. bonding. For example, the 1,500-fold purified mitogen may be applied to a SynChropak RP-8 column (SynChrom).

The high concentration of acetonitrile required to elute the active peaks from the reverse phase column suggests that the mitogen is a hydrophobic molecule.

It will be appreciated that the compound of interest is defined in terms of mitogenic activity, as revealed for example in the mitogenesis assay described below. Accordingly the compound of interest can be reduced to subunits, truncated, contain amino acid substitutions, be modified to contain less or more carbohydrate and the like so long as mitogenic activity is maintained. Mitogenic activity is defined as capable of stimulating DNA synthesis in a mitogenesis monitoring system, such as the endothelial cell assay described herein, as compared to a baseline level wherein no compound of interest is exposed to said monitoring system.

The substantially pure mitogen can be used as a treatment modality in the form of a pharmaceutic preparation. The medicament comprises an effective amount of the mitogen and a pharmaceutically acceptable carrier, diluent or excipient. The effective amount of a mitogen can be determined using art-recognized methods, such as by establishing dose-response curves in suitable animal models, preferably non-human primates, and extrapolating to human or by determining effectiveness in clinical trials.

The mitogen can be administered in a variety of ways such as orally, parenterally and topically. The dosage, number of treatments and duration of treatment will vary according to the individual and the severity of the disorder.

The medicament can take a variety of forms such as tablets, capsules, bulk or unit dose powders or granules; may be contained within liposomes; or may be formulated into solutions, emulsions, suspensions, ointments, pastes, creams, gels, foams or jellies. Parenteral dosage forms include solutions, suspensions and the like. The medicament is likely to contain any of a variety of art-recognized excipients, diluents, fillers etc. Such subsidiary ingredients include disintegrants, binders, lubricants, surfactants, emulsifiers, buffers, moisturizers, solubilizers and preservatives. The artisan can configure the appropriate formulation comprising the mitogen and seeking guidance from numerous authorities and references such as Goodman & Gilman's *The Pharmaceutical Basis of Therapeutics* (6th ed., Goodman et al., eds., MacMillan Publ. Co., N.Y., 1980).

The mitogen finds therapeutic utility in circumstances that require cell growth, such as wound healing. In the case of epidermal abrasion, laceration, puncture or other lesion, the mitogen can be administered directly to the wound site in the form of, for example a liquid, gel or cream, in established effective amounts. The mitogen preparation can be administered singly or in a plurality of treatments.

In body sites that are characterized by continual cell growth or require cell growth because of injury or dysfunction and are not as accessible as skin, the mitogen can be administered in a suitable fashion to assure effective local concentrations of the mitogen. For example, the mitogen may be injected in a depot or adjuvant, carried in a surgically situated implant or reservoir that slowly releases a fixed amount of mitogen over a period of time or may be complexed to recognition molecules with the capability of binding to the site requiring the mitogen.

The present invention will be described in further detail in the non-limiting examples to follow.

EXAMPLE 1

To obtain a crude extract the method taught by Sperti (supra) was used. Briefly, while stirring, 1636 kg of fresh live Baker's yeast (*Saccharomyces cerevisiae*) were added to a jacketed reaction vessel containing 1703 L of methanol-denatured alcohol. The mixture was gently agitated and heated under reflux for 3 hours at 70° C.±2° C. While continuing to stir, the mixture was cooled to 50° C. and 114 kg of celite were added. After cooling the mixture to 35° C., it was vacuum filtered. Then 10 kg of charcoal were added to the filtrate, stirred 1 hour at ambient temperature, then 7.7 kg of celite were added and the mixture was vacuum filtered. The alcohol was removed under vacuum to obtain an aqueous solution which had a specific gravity of approximately 1.18 g/ml at 25° C. The solution was agitated slowly and heated at 90° C. for four hours, cooled to 30°–35° C. and vacuum filtered through a heated celite filter cake made from 68 kg of celite and 300 gallons of deionized water. To the filtrate were added 7.7 kg of celite and after filtering the solution was concentrated under vacuum to a specific gravity of 1.24–1.30 g/ml. The concentrate was heated to 40°–41° C. and passed through a filter press containing a filter cake made from 7.7 kg celite and 25 gallons of deionized water. The resulting dark brown syrup with a yeasty odor had a specific gravity of 1.25–1.30 g/ml and contained approximately 45–60% solids.

EXAMPLE 2

A yeast derived alcohol extract comprising a viscous brown aqueous syrup of Example 1 was obtained from Whitehall Laboratories, Hammonton, N.J. The syrup was diluted with two volumes of distilled water and clarified by centrifugation for one hour at 43,000×g. The clarified supernatant was retrieved.

EXAMPLE 3

The sample of Example 2 was placed into a porous membrane tubing with a molecular weight cut-off of 1000 which was then suspended in four liters of dialysis buffer (10 mM sodium phosphate, pH 7.0, 10 mM sodium chloride). (Dialysis membranes are available commercially from a number of sources, such as Spectrum Medical Industries, Inc., Los Angeles, Calif. which distributes the SPECTRA-POR ® line of dialysis membranes. A suitable SPECTRA-POR ® dialysis tubing is SPECTRA-POR ® 6 with a molecular weight cut-off of 1,000. Generally, the tubing is shipped in an aqueous solution containing a preservative such as sodium azide. The dialysis tubing is rinsed extensively with deionized or distilled water or buffer to remove all traces of preservative. One end of the tubing is clipped or sealed, the sample is added to the tube and the remaining end of the tube is sealed.) The beaker containing buffer and the dialysis bag was then placed on a magnetic stirrer and was maintained generally at 4° C. Buffer was replaced periodically and dialysis was allowed to proceed at least overnight.

Dialysis of the clarified extract generally yields about a 16-fold purification of the mitogen. Presence of and activity of the mitogen was determined using the bioassay referred to above and further described in the next Example.

EXAMPLE 4

Mitogen activity was monitored using an in vitro assay. Fetal bovine heart endothelial cells were obtained from the American Type Culture Collection (CRL 1395, a publicly available non-patented cell line). The cells were maintained in Dulbecco's modified Eagle's medium supplemented with 10% fetal bovine serum and 100 ng/ml fibroblast growth factor (complete medium). Cells were passed at a split ratio of 1:3 twice a week.

The cells were seeded in 96 well microtiter plates at about 8,000 cells per well in a volume of 100 $\mu$l per well. After the cells attached, the complete medium was replaced with 150 $\mu$l of medium containing 0.5% serum. The cells were incubated for at least 48 hours under those conditions. Then 50 $\mu$l of test agent was added to replicate wells. The cells were exposed to the test agent at 37° C. for approximately 18 hours. Tritiated thymidine at a concentration of 4 $\mu$Ci/ml in a volume of 50 $\mu$l was added to each well, yielding a final volume of 200 $\mu$l and a final concentration of 1 $\mu$Ci/ml. The mixture was incubated at 37° C. for four hours. The cells were then washed with phosphate buffered saline and then lysed with 0.1% sodium dodecyl sulphate and 1 mM EDTA. The lysates were harvested on filter disks using twelve washes of cold 5% trichloroacetic acid. The filtered disks were removed and placed into scintillation vials to which an appropriate cocktail was added. The samples were then read in a liquid scintillation counter.

Data from a representative experiment are set forth in FIG. 1.

EXAMPLE 5

The dialyzed extract at physiologic pH was acidified to pH 3.5 by addition of dilute hydrochloric acid. After an incubation of one hour at 4° C., the precipitate was separated by centrifugation. The precipitate was dissolved in phosphate buffered saline.

Dialysis and Acid precipitation yielded about a 240-fold purification of the clarified mitogen as determined by bioassay.

EXAMPLE 6

The FPLC system is distributed by Pharmacia and includes liquid chromatography equipment such as pump, UV monitoring units, fraction collector and recorder. A Superose 12 HR 10/30 prepacked column was used. Chromatography was done essentially according to the manufacturer's recommendations.

Briefly, the pump's lines and column were washed with buffer, for example, 500 mM KCl, 50 mM Tris, pH 8 and 0.02% sodium azide prepared in HPLC grade water. The mitogen preparation was filter sterilized through a 0.22 micron filter prior to being applied to the column. Tryptophan was used as an internal standard. (The tryptophan stock solution was prepared at a concentration of 2.5 mg/ml in the buffer described above. One aliquot was used per day.) The sample containing mitogen and tryptophan was applied to the column and fractions were collected. Generally, the tryptophan standard eluted at about 28 ml.

Figure 2:
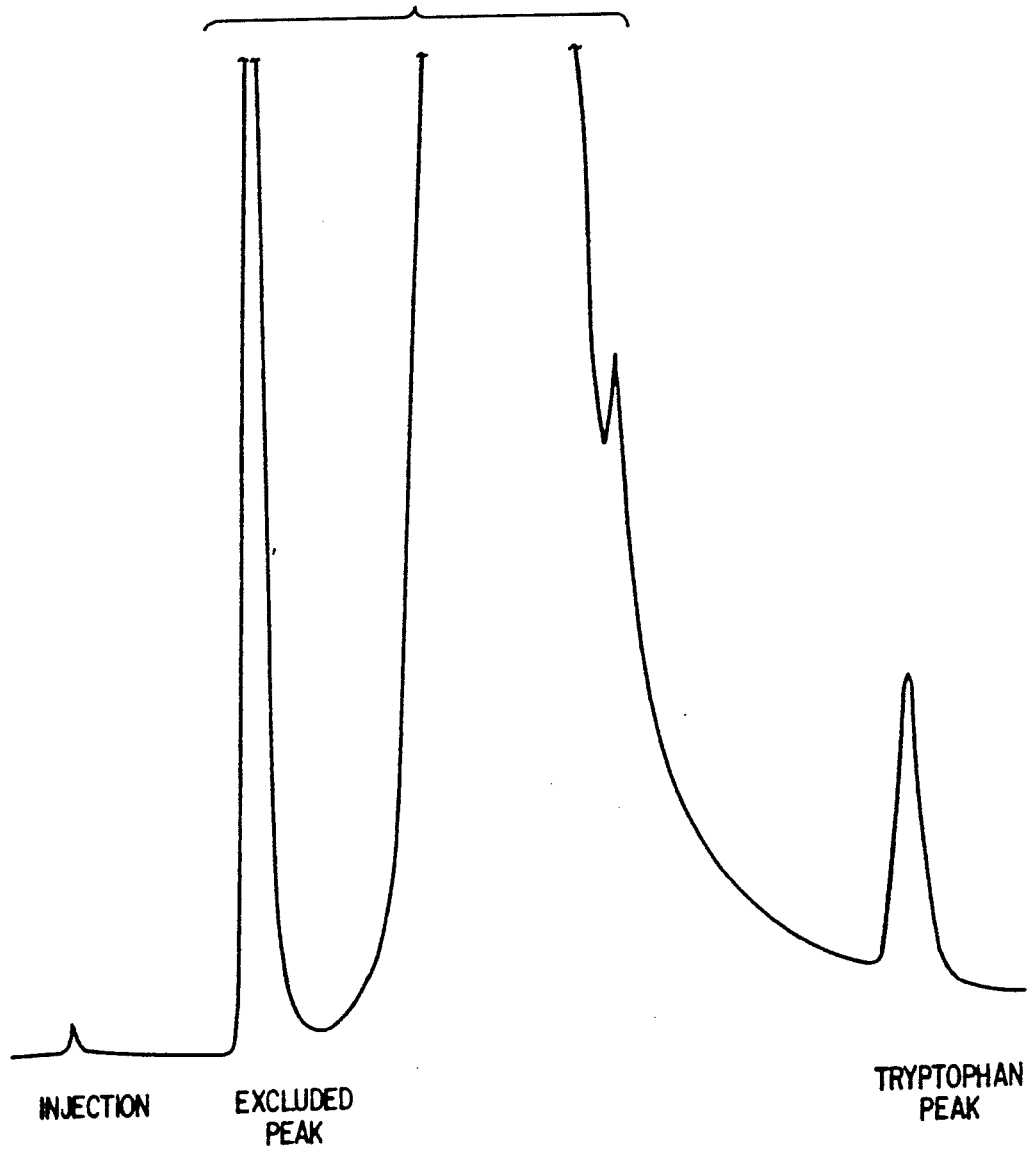
FIG. 2 depicts a chromatogram of 280 nm absorbable material eluted from a Superose 12 HR 10/30 column. The particulars are 2.0 AU Full scale wherein 300 μl of a sample (330 μl of dialyzed live yeast cell derivative (LYCD) and 10 μl of 2.5 mg/ml tyrptophan) were applied to the column at a flow rate of 0.5 ml/min using a buffer comprising 0.05M Tris, pH 8.0, 0.5M KCl and 0.02% NaN$_3$.

Normally, using the UV monitor at 280 nm with a flow rate of 0.5 ml/min, three peaks were found. There was first the small excluded peak that contained mitogenic activity, a large discrete second peak, and finally a discrete third peak comprising the tryptophan standard (FIG. 2).

Fractions were collected in plastic tubes and those found to contain mitogenic activity, as determined by expression of mitogenic activity in the bioassay, were pooled and lyophilized. Lyophilization was done using standard procedures. Briefly, the samples were aliquoted in small volumes, frozen and placed under vacuum. Samples were kept at reduced temperature after desiccation.

EXAMPLE 7

Optionally, the mitogen of Example 4 was purified over TSK size exclusion resins. The mitogen bound to a TSK Bio-Sil column in a buffer comprising 45% acetonitrile, 0.1% trifluoroacetic acid solution. The mitogen eluted slightly later than the main inactive peak.

The acid precipitate of the mitogen was purified approximately 9-fold by chromatography over a TSK Bio-Sil column in a solution of 60% acetonitrile and 0.1% trifluoroacetic acid. TSK chromatography, however, did not significantly purify the Superose 12 product. Again activity was monitored using the bioassay.

EXAMPLE 8

Figure 3:
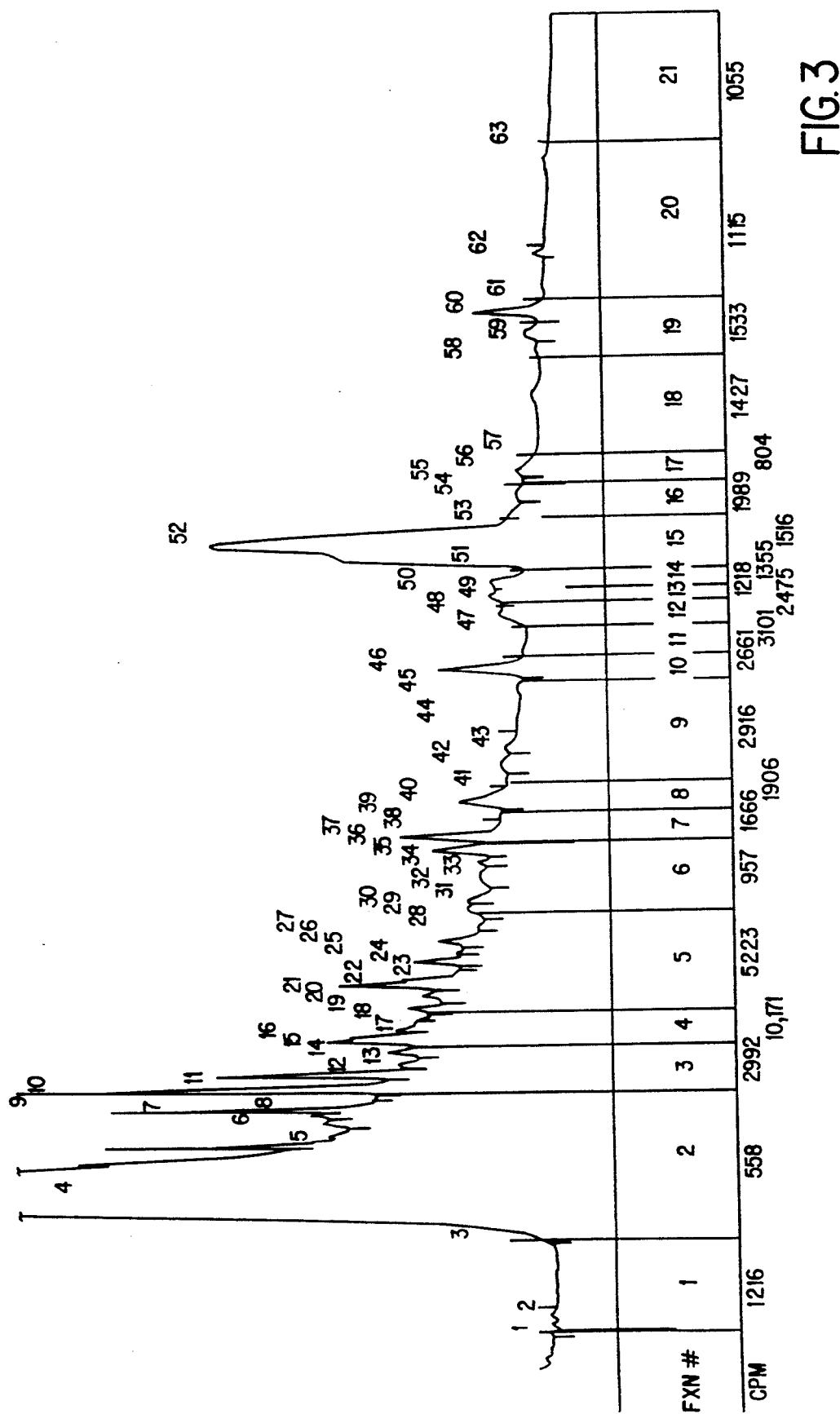
FIG. 3 depicts a chromatogram of proteins obtained from the Superose 12 column and passed over a reverse phase C8 column. The solid line is the absorbance at 280 nm. The numbers above the trace indicate the time of elution. Please refer to the following key.

Reverse phase columns can often effect very high resolution purification of proteins based on differences in hydrophobicity. The active fraction following Superose 12 chromatography was applied to a C8 reverse phase column that was equilibrated with aqueous buffer comprising 95% of 0.05 M triethylammonium acetate, pH 5.6 and 5% acetonitrile. The acetonitrile concentration was increased to 45% over five minutes and then increased again to 100% over ninety minutes. Eluted proteins were monitored by absorbance at 280 nm. The result was a large number of peaks (FIG. 3). Mitogenic activity, as determined by the bioassay, was limited to specific groups of peaks. Fractions were collected, the acetonitrile was removed by evaporation with a stream of nitrogen and the aqueous solutions were lyophilized.

Publications and references referred to and recited herein are expressly incorporated by reference.

While preferred embodiments of the instant invention have been described, it will be apparent to those skilled in the art that many changes and modifications can be made without departing from the spirit of the invention. The described embodiments are thus to be considered illustrative and not restrictive. The scope of the invention is, therefore, indicated by the appended claims rather than by the foregoing description. All changes that come within the meaning and range of equivalency are to be embraced within the scope of the invention.

What is claimed is:

1. A substantially pure mitogen obtained by alcohol extraction of live yeast and having a molecular weight of greater than about 300,000 daltons using gel filtration chromatography which
    a) retains mitogenic activity on bovine endothelial cells following a 5 minute exposure to 100° C.;
    b) retains mitogenic activity on bovine endothelial cells following lyophilization;
    c) stable at pH of 7 or greater;
    d) elutes in reverse phase chromatography with a buffer comprising at least 50% acetonitrile; and
    e) is reversibly precipitated at a pH of 4 or lower.

2. The mitogen of claim 1 wherein the molecular weight is greater than about 600,000 daltons.

3. The mitogen of claim 1 wherein said yeast is of the genus Sacharomyces.

4. The mitogen of claim 3 wherein said yeast is Saccharomyces cerevisiae.

5. A mitogen obtained from live yeast and have a molecular weight of greater than about 300,000 daltons using gel filtration chromatography which
    a) retains mitogenic activity on bovine endothelial cells following a 5 minute exposure to 100° C.;
    b) retains mitogenic activity on bovine endothelial cells following lyophilization;
    c) stable at pH of 7 or greater;
    d) elutes i reverse phase chromatography with a buffer comprising at least 50% acetonitrile; and
    e) is reversibly precipitated at a pH of 4 or lower;
and is prepared by the process of
    a) heating mixture of fresh live yeast and methanol-denatured alcohol;
    b) filtering said mixture to produce a filtrate; and
    c) removing said alcohol to produce an aqueous concentrate.

6. The mitogen of claim 5 which process further comprises a purifying step comprising dialyzing said aqueous concentrate to produce a dialysate in a tubing with a molecular weight cut-off between of about 1000 to about 500,000.

7. The mitogen of claim 6 wherein said purifying step further comprises exposing said dialysate to a pH of 4 or less to produce a precipitate and dissolving said precipitate in a buffer.

8. The mitogen of claim 6 wherein said purifying step further comprises exposing said dialysate to a size exclusion gel matrix with an exclusion limit of about 300,000 daltons and collecting the void volume.

9. The mitogen of claim 7 wherein said purifying step further comprises exposing said dissolved precipitate to a size exclusion gel matrix with an exclusion limit of about 300,000 daltons and collecting the void volume.

10. The mitogen of claim 8 wherein said purifying step further comprises exposing said void volume to a silica gel exclusion matrix.

11. The mitogen of claim 9 wherein said purifying step further comprises exposing said void volume to a silica gel exclusion matrix.

12. A parmaceutical composition for stimulating cell proliferation comprising a therapeutically effective amount of the mitogen of any one of claims 1, 2, 3, 4, 5, 6, 7, 8, 9, 10 or 11 and a pharmaceutically acceptable carrier diluent of excipient.

13. The pharmaceutical compositions of claim 12 comprising a topical dosage form.

14. A method treating the epidermis to promote epidermal cell or tissue growth or repair comprising administering to an individual in need thereof a therapeutically effective amount of the pharmaceutical composition of claim 12.

15. The method of making a mitogen of claim 1 comprising:
    a) heating a mixture of fresh live yeast and methanol-denatured alcohol;
    b) filtering said mixture to produce a filtrate;
    c) removing said alcohol from the filtrate to produce an aqueous concentrate;
    d) diluting said concentrate to produce an aqueous solution;
    e) centrifuging said aqueous solution to produce a clear solution; and
    f) dialyzing said clear solution to produce a dialysate.

16. The method claim 15 wherein said yeast is of the genus Saccharomyces.

17. The method of claim 16 wherein said yeast is Saccharomyces cerevisiae.

18. The method of claim 15 wherein said dialyzing step comprises a dialysis membrane with a molecular weight cut-off of at least 1000.

19. The method of claim 18 wherein said dialysis membrane has a molecular weight cut-off of about 500,000.

20. The method of claim 15 which further comprises exposing said dialysate to a pH of less than 4 to produce a precipitate and dissolving said precipitate in a buffer to produce a dialysate solution.

21. The method of any one of claims 15-20 which further comprises treating said dialysate or dialysate solution with a size exclusion gel filtration chromatography matrix.

* * * * *